United States Patent [19]

Castellini

[11] Patent Number: 4,839,004
[45] Date of Patent: Jun. 13, 1989

[54] METHOD AND AN APPARATUS FOR COLD STERILIZATION OF SURGICAL INSTRUMENTS, IN PARTICULAR DENTAL SURGERY INSTRUMENTS

[75] Inventor: Franco Castellini, Bologna, Italy

[73] Assignee: Castellini, S.P.A., Bologna, Italy

[21] Appl. No.: 159,718

[22] Filed: Feb. 24, 1988

[30] Foreign Application Priority Data

Feb. 27, 1987 [IT] Italy .................................. 3365 A/87

[51] Int. Cl.⁴ .............................................. C25B 1/26
[52] U.S. Cl. ..................................... 204/128; 204/94; 204/95; 204/98; 204/228; 204/284; 204/271; 422/22; 422/37; 422/116
[58] Field of Search ................................... 204/94–95, 204/98, 128, 130, 140, 228, 259, 284–285, 271; 422/22, 37, 116, 186, 186.04, 905

[56] References Cited

U.S. PATENT DOCUMENTS

| | | | |
|---|---|---|---|
| 1,217,643 | 2/1917 | Schneider | 204/271 |
| 1,702,767 | 2/1929 | Curtis | 204/271 |
| 2,121,875 | 6/1938 | Kruse et al. | 204/271 |
| 2,180,668 | 11/1939 | Delavella et al. | 204/95 |
| 2,701,790 | 2/1955 | Goument | 204/95 |
| 3,219,563 | 11/1965 | Collins et al. | 204/95 |
| 4,171,256 | 10/1979 | Themy | 204/239 |
| 4,201,651 | 5/1980 | Themy | 204/217 |
| 4,316,787 | 2/1982 | Themy | 204/242 |
| 4,710,233 | 12/1987 | Hohmann et al. | 134/1 |

*Primary Examiner*—John F. Niebling
*Assistant Examiner*—David G. Ryser
*Attorney, Agent, or Firm*—Laff, Whitesel, Conte & Saret

[57] ABSTRACT

The method and apparatus are designed to permit of sterilizing surgical instruments by inducing electrolysis in a water solution having pH-value of between 5 and 7.5 and a concentration of chloride ions between 0.45 and 0.85 g/l; the electrolyte is buffered with each sterilizing cycle, and its condition monitored continuously.

20 Claims, 1 Drawing Sheet

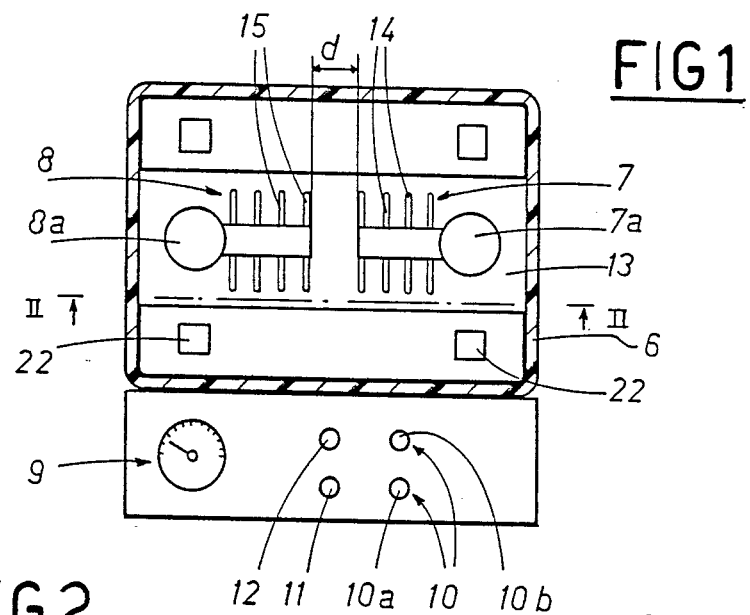
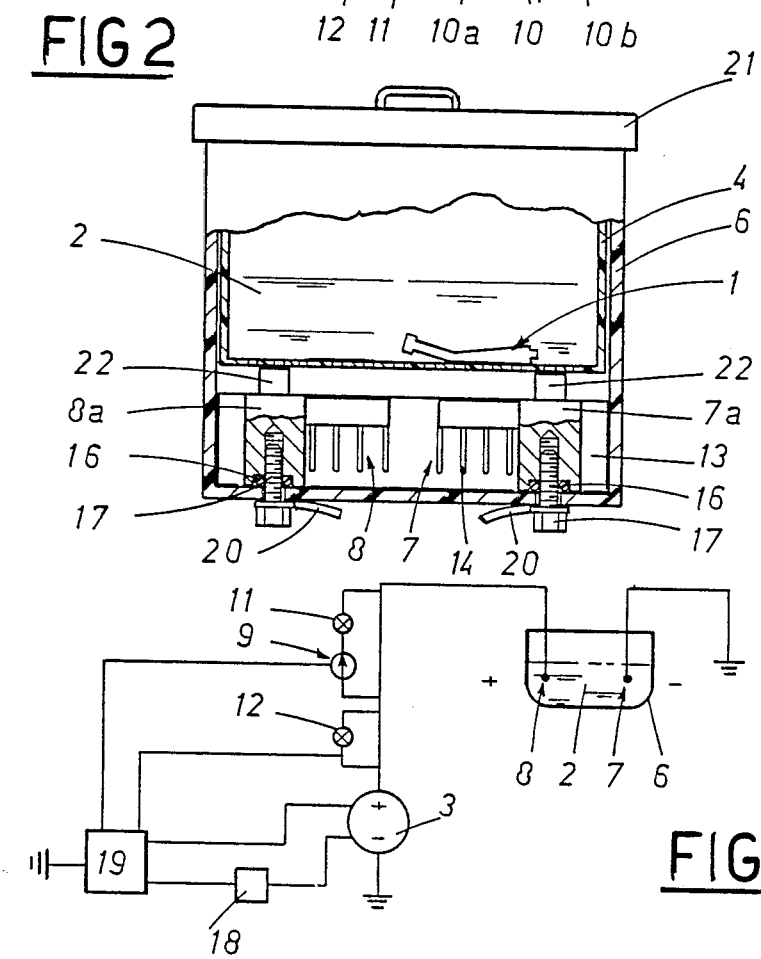

METHOD AND AN APPARATUS FOR COLD STERILIZATION OF SURGICAL INSTRUMENTS, IN PARTICULAR DENTAL SURGERY INSTRUMENTS

BACKGROUND OF THE INVENTION

The invention relates to a method of sterilizing surgical instruments under cold conditions, in particular dental surgery instruments, and to an apparatus for the implementation of such a method.

The necessity for sterilizing surgical instruments is one of great importance, and most especially in environments where such instruments are brought directly or indirectly into contact with a major carrier of infection such as blood, saliva etc. . . . Such is the case in environments where even small surgical operations are carried out, as for example, the dental surgery.

The sterilization of surgical instruments (that is, the entire range of items including handles, bistouries, tweezers, implements etc.) is essential, especially in situations where several patients are treated by a dentist within a short period of time, to the end of avoiding any transmission of infection from one patient to another.

The current state of the art in sterilization of surgical instruments offers three different methods.

A first method makes use of gamma rays. This is a familiar technique already used in the sterilization of throw-away syringes, and notably effective from the standpoint of the results that are obtainable; nonetheless, one has the drawback that the apparatus required for its implementation is costly, and none too practical inasmuch as operation is necessarily subject to certain precautions.

In the second method, sterilization takes place in an autoclave; the instruments are generally enclosed in a special bag that is fastened and placed inside the pressure vessel, submerged in a suitable liquid in certain instances. The sterilization is brought about in this case by the high temperature with which the instruments are invested.

Apparatus for this second method is less costly and more practical, though considerable disadvantages are encountered, connected with the high temperature to which the instruments are subjected, and the time needed to effect a sterilization. The high temperature can in fact produce deformation in an instrument fashioned with parts in plastic, to the extent that its usefulness is affected, and in the case of a bistoury, may counteract the effects of hardening and cause the cutting edge to become dulled.

The third method in question envisages immersion of the instruments in a solution of 2%-glutaraldehyde for a period of not less than three hours duration, in which case a substantial supply of instruments becomes necessary if work is to proceed reasonably uninterrupted.

Accordingly, the object of the invention is to set forth a method that will enable sterilization to be effected using low-cost, functional apparatus, and without any of the drawbacks mentioned above.

SUMMARY OF THE INVENTION

The stated object is achieved with a method and a relative apparatus according to the invention, with which it is possible to sterilize instruments in cold conditions, namely, by generating active chlorine at a given concentration.

One advantage of the invention consists essentially in the fact that sterilization is accomplished by a simple and safe method, since electrolysis occurs at ultra-low concentration, at a controlled pH value, and with a high relative production of chlorine.

Another advantage given by the invention is that of the speed of the sterilizing operation. All that is required is to place the instruments in a receptacle and immerse the receptacle in the electrolyte; the cycle is then standard, effected automatically and with all the variable factors in play accounted for.

A further advantage of the method disclosed is that it ensures faultless operation and a fully effective sterilization, without occasioning any damage to the instruments.

BRIEF DESCRIPTION OF THE DRAWINGS

The invention will now be described in detail, by way of example, with the aid of the accompanying drawings, in which:

FIG. 1 is a plan of the apparatus according to the invention, not to scale, showing the tank without its lid and without the receptacle in which surgical instruments are placed for sterilization;

FIG. 2 is the section through II—II in FIG. 1, showing the apparatus in its entirety, ready to implement a sterilization cycle;

FIG. 3 shows a block diagram of electrical components forming part of an apparatus as in FIGS. 1 and 2.

DESCRIPTION OF THE PREFERRED EMBODIMENT

The method of sterilizing instruments according to the invention comprises the steps of:

immersing the instruments 1 totally in a bath of electrolyte 2 consisting in a water solution having pH-value of between 5.0 and 7.5 and a concentration of chloride ions between 0.45 and 0.85 g/l;

inducing electrolysis for a period of set duration to the end of forming active chlorine;

immediately removing the receptacle 4, rinsing at least those instruments fashioned in materials other than plastic, and drying off the instruments 1.

To generate active chlorine to best effect, electrolysis occurs according to the invention with electrical energy supplied at 8V d.c.; the voltage remains fixed, whereas the rectified and stabilized direct current is variable in absolute value so as to match the absorption of the electrolyte bath.

The electrolytic reactions that take place are the self-same classic reactions as those induced in the manufacture of chlorine, hydrogen and caustic soda by industrial methods—i.e. with chlorine produced at the anode, and hydrogen at the cathode.

The aforementioned concentration of Cl— chloride ions in the electrolyte will be the lowest possible in order to avoiding damage to the instruments 1 being sterilized, and sufficient to give place, in operation, to a concentration of active chlorine in the tank quantifiable at 100 ppm ±10%.

It is thus the active chlorine that constitutes the sterilizing agent; to ensure maximum effectiveness however, the chlorine needs to operate in an acid environment, or at all events, one having a pH-value lower than 7.5, as aforementioned.

In such conditions, more exactly, the chlorine is present as HOCl, considered to be the most active, whereas above pH 7.5, a separation occurs into OCl—, occasioning a drastic loss of sterilizing power. On the other hand, too low a pH-value can adversely affect the material in which the instruments happen to be fashioned, and accordingly, the electrolyte 2 is made to operate within the margins of pH 5 to 7.5 as aforementioned.

This ideal condition is subject to change during operation, however, due to the continual formation of alkaline hydrate at the cathode, and if provision is not made to compensate for such a contingency, the pH-value will rise quickly to 8, and higher.

Accordingly, use is made of an electrolyte 2 which, at the outset, is a water solution having chloride ions in a concentration of between 0.5 and 0.8 g/l and a pH-value no greater than 4, and this solution is conditioned prior to effecting a given number of sterilization cycles. With conditioning accomplished, a further solution is admixed to the electrolyte with each sterilization cycle effected—i.e. a buffer, which is able to offset the rising alkaline content and maintain the pH-value at less than 7.

In addition to the buffer solution, a calculated quantity of Cl— chloride ions is introduced so as to compensate for the reduced proportion of chloride ions in the electrolyte 2 and hold the concentration of chlorine at a steady level.

Referring now to FIG. 2, apparatus suitable for implementing the method according to the invention comprises:
- a receptacle 4, in which instruments 1 requiring sterilization are contained;
- a tank 6, with a removable lid, accommodating the receptacle 4 and filled with electrolyte 2;
- a pair of electrodes 7 and 8, situated internally of a housing 13 incorporated into the base of the tank 6 beneath the receptacle 4 and connected to a generator 3 of electric current;
- a timer 18, capable of switching the generator 3 on and off;
- monitoring and control means 9, 10, 11, 12 and 19 capable of switching on the timer 18 and switching off the generator 3.

The receptacle 4 and tank 6 are both embodied in a material unaffected by the chlorine, such as ABS or PVC, and the receptacle 4 will be perforated at least at bottom. These perforations take the form of a set of holes 5 in the example of FIG. 1, though the bottom of the receptacle 4 might equally well be embodied in mesh, allowing the electrolyte a better circulation. The tank 6 will be of some 15 liters capacity, and shaped to accommodate the receptacle 4 with its bottom raised a suitable height from the base.

Comparing FIGS. 1 and 2, it can be seen that the tank 6 appears as a parallelepiped with a centrally located sunken housing 13 serving to accommodate two electrodes, negative 7 and positive 8. Accordingly, the external profile of the tank 6 (considered in its entirety) exhibits two recesses, one either side of the central housing 13; in ultimate embodiment of the apparatus, the recesses will in fact serve to accommodate the generator 3 and the monitoring and control means 9, 10, 11, 12 and 19, though these are positioned to one side of the tank 6 in FIG. 1 so as to provide a clearer illustration.

22 denotes a set of blocks located at the base of the tank 6; it is on these blocks that the bottom of the receptacle 4 is made to rest, thus allowing the electrolyte 2 to circulate freely beneath.

According to the invention, the tank 6 contains an electrolyte 2 consisting in a water solution of the following preferred composition:
- NaCl 0.75 ... 1.4 g/l, equivalent to a concentration of
 - Cl— chloride ions between 0.45 and 0.85 g/l
- Citric acid 0.00 ... 1.00 g/l
- Sodium citrate 0.00 ... 1.00 g/l
- Demineralized $H_2O$ by volume
- pH-value 5.0 ... 7.5

Given that the chloride ion is the donor, it becomes possible to express the anion concentration only, provided that in replacing sodium, one of the alkali or alkaline earth metals is utilized.

In whichever instance, the basic values must remain:
- Cl— chloride ions: 0.45 ... 0.85 g/l
- pH value 5.0 ... 7.5

Thus, the use of two distinct solutions is envisaged in implementing a method according to the invention: the one for initial conditioning of the electrolyte, the other for subsequent buffering. In a preferred formulation, the conditioner will be a water solution having a pH-value of no more than 4 and a concentration of Cl— chloride ions between 0.5 and 0.75 g/l. The buffer solution is likewise a water solution, but with a concentration of Cl— chloride ions of between 0.005 and 0.01 g/l, and an acidifying element the quantity of which will be sufficient to ensure that the pH-value of the electrolyte 2 stays within the limits stated.

An advantageous acidifying element would be citric acid, at a concentration of 0.045 ... 0.65 g/l.

The negative electrode or cathode 7, is embodied in activated titanium, and the positive electrode, or anode 8, in titanium; both consist in a plurality of parallel screens denoted 14 and 15 respectively.

The surface area of the screens 14 and 15 needs to be generous in order to guarantee a better and more effective electrolysis; preferred dimensions are 0.8 ... 1.2 $dm^2$ per liter of electrolyte for the cathode, and 0.4 ... 0.6 $dm^2/l_{el'te}$ for the anode.

The two sets of screens 14 and 15 are vertically disposed and set apart at an advantageous distance d (see FIG. 1) between the two electrodes 7 and 8; the distance d most suitable is approximately 3 mm.

7a and 8a denote a pair of horizontal, coaxially disposed round section bars to which the screens 14 and 15 are fastened along one edge, say, by welding; these bars will be fashioned in the same material as the screens themselves.

Each bar 7a and 8a bends downwards at one end, and terminates in a butt that affords a tapped hole encircled by a seat in which to lodge a seal 16. 17 denotes either one of two fixing screws freely insertable through holes in the base of the central housing 13; each screw 17 engages in the hole of a relative bar 7a and 8a, and serves also to clamp the the end of a relative lead 20 connecting with the generator 3. Thus the screws 17 perform a dual role, tightening the bars 7a and 8a against the base of the tank 6 and rendering the holes watertight by compressing the relative seals 16, and connecting the electrodes 7 and 8 to their power source, the generator 3.

The generator 3 produces direct current, rectified and stabilized, at an unvarying 8 volts; the absolute value of the current component, however, is variable to match the conductivity of the electrolyte.

According to the invention, monitoring and control means used in the apparatus comprise:
- a pair of buttons 10 serving to activate the apparatus;

an instrument serving to measure the absorption level of the electrolyte 2 consisting, for example, in an ammeter 9, which is wired in parallel to the main power circuit supplying the electrodes 7 and 8 via a shunt in order to increase its range;

two acoustic and/or luminous indicators 11 and 12, the first wired in series with the ammeter 9 and serving to signal overabundant absorption of current by the electrolyte 2, the second wired in parallel with the power circuit supplying the electrodes 7 and 8 and serving to signal insufficient absorption;

a timer 18 serving to switch the generator 3 on and off;

a controller, denoted 19, which may be programmable or otherwise.

The sterilization procedure will now be described, adopting the method according to the invention, and utilizing an apparatus as described above for its implementation, assuming switch-on at the start of surgery hours.

The user first pours in a prescribed quantity of initial conditioner solution into the clean tank 6, covers the apparatus with the lid 21, and depresses the "condition" button 10a, whereupon the relative process will be set in motion. This preparatory step has a set duration of 12 minutes approx, which is clocked by the timer 18, and visual evidence of its progress is given by an indicator (not illustrated); on completion, another indicator lights up to signal "stand-by" status, and the apparatus is ready to sterilize. Termination of the conditioning process has the effect of enabling the controller 19 for subsequent sterilization, and the cycle can thus be activated at any given moment. Sterilization remains possible as long as the controller 19 is enabled, and the electrolyte will stay "conditioned" for up to four hours without being used.

The steps of the sterilizing cycle occur as follows. Instruments 1 to be sterilized are washed in accordance with legal requirements and placed in the receptacle 4, whereupon the prescribed quantity of buffer solution is poured into the tank 6, and the receptacle 4 is lowered into the tank and set on the blocks 22.

Having made certain that the instruments are fully immersed in the electrolyte 2, the user can replace the lid 21 and depress the "sterilize" button 10b. Current now flows from the generator 3 for a set duration (2 . . . 5 minutes), controlled by the timer 18. A further luminous indicator confirms that sterilization is in process, and completion of the sterilization cycle is signalled by yet another indicator, as well as by an acoustic signal.

With sterilization completed, the receptacle 4 is removed without delay, and the instruments rinsed off and dried. Rinsing is indispensable for those instruments fashioned in material that might be susceptible to oxidation (even the stainless steel specifically formulated for surgical implements), though not imperative for plastic materials.

At this juncture, the apparatus is ready for another sterilization cycle.

The maximum current indicator 11 will light up in the event that the electrolyte 2 becomes saturated with repeated cycles, or that an error is detected in the formulation of fresh electrolyte 2, that is, registering too high a concentration for whatever reason, accidental or otherwise. Should the maximum current indicator 11 light up, the electrolyte 2 must be emptied out and replaced with fresh.

The indicator denoted 12, on the other hand, will light up the event that there is insufficient current absorbed. This can occur if the electrolyte is prepared with a quantity of conditioner less than that prescribed, or if the anode 8 suffers major damage; in either instance, the apparatus would not be able to perform dependably.

In an alternative embodiment of the apparatus, the controller 19 might comprise a CPU, in which case one button 10 only would suffice to set the cycle in motion.

What is claimed:

1. A method for the cold sterilization of surgical instruments comprising:
    immersing the instruments in a bath of a water electrolyte solution having pH-value of less than 7.5 and a concentration of chloride ions between 0.45 and 0.85 g/l;
    without having the instruments contacting an electrode, or anode inducing electrolysis of the electrolyte for a predetermined time whereby active chlorine is generated in the electrolyte and the instruments are sterilized.

2. A method as in claim 1 comprising an initial step of buffering the electrolyte by admixing a solution containing chloride ions at a concentration of between 0.005 and 0.01 g/l, and an acidifying element sufficient in quantity of maintain the pH-value of between 5.0 and 7.5.

3. A method as in claim 2 wherein the acidifying element is citric acid, present in a concentration of between 0.045 and 0.065 g/l.

4. A method as in claim 1 comprising an initial step of conditioning whereby electrolysis is induced for a predetermined time on an electrolyte which consists of a water solution with pH-value no greater than 4 and a concentration of chloride ions between 0.5 and 0.75 g/l.

5. A method as in claim 1, wherein the electrolyte solution has a pH of between 5.0 and 7.5 and the step of inducing electrolysis continues for between 2 and 5 minutes.

6. A method as in claim 4, wherein the duration of the conditioning step is approximately 12 minutes.

7. A method as in claim 1 wherein the instruments are placed in a removable receptacle and comprising the final steps of
    removing the instruments from the bath of electrolyte,
    rising at least such instruments as are fashioned in materials other than plastic, and
    drying the instruments.

8. A method for cold sterilization of surgical instruments comprising the steps of:
    immersing the instruments in a bath of a water electrolyte solution having pH-value of between 5.0 and 7.5 and a concentration of chloride ions between 0.45 and 0.85 g/l;
    inducing electrolysis of the electrolyte for a predetermined time by utilizing electrical power supplied at 8V d.c., which has a voltage component and a rectified and stabilized direct current and which the voltage component remains constant, and the rectified and stabilized direct current component is variable in absolute value to match the conductivity of the electrolyte.

9. A method as in claim 8 comprising an initial step of buffering the electrolyte by admixing a solution containing chloride ions at a concentration of between 0.005 and 0.01 g/l, and an acidifying element sufficient in quantity to maintain the pH-value of between 5.0 and 7.5.

10. A method as in claim 9 wherein the acidifying element is citric acid, present in a concentration of between 0.045 and 0.065 g/l.

11. A method as claim 8, comprising the final steps of removing the instruments from the bath of electrolyte,
rising at least such instruments as are fashioned in materials other than plastic, and
drying the instruments.

12. A method as in claim 8, wherein the step of inducing electrolysis continues for a duration of between 2 and 5 minutes.

13. A method as in claim 8 comprising an initial step of
conditioning whereby electrolysis is induced for a predetermined time on an electrolyte which consists of a water solution with pH-value no greater than 4 and a concentration of chloride ions between 0.5 and 0.75 g/l.

14. A method as in claim 13, wherein the duration of the conditioning step is approximately 12 minutes.

15. Apparatus for the cold sterilization of surgical instruments, comprising:
a receptacle, perforated at least at bottom, in which the instruments requiring sterilization are contained;
a tank, accommodating the receptacle, which has a removable lid and is of capacity such as to contain a predetermined quantity of electrolytes;
a pair of electrodes, situated internally of a housing incorporated into the base of the tank, beneath the receptacle, and connected to a generator of electric current;
a timer, capable of switching the generator on and off;
means for detecting excessive or insufficient current absorption;
monitoring, control and indicator means capable of switching on the timer, and of switching off the generator upon detection of excessive or insufficient current absorption through the electrolyte.

16. Apparatus as in claim 15, wherein the electrodes each consist in a plurality of parallel screens rigidly attached to a respective bar that is fastened to the tank.

17. Apparatus as in claim 16, wherein the negative and positive electrodes are embodied in activated titanium and titanium, respectively.

18. Apparatus as in claim 16, wherein the screens of the negative and positive electrodes exhibit surface areas of between 0.8 and 1.2 and 0.4 and 0.6 $dm^2$ respectively, per liter of electrolyte.

19. Apparatus as in claim 16, wherein the electrodes are disposed parallel one to the other, with their respective screens set approximately 3 mm apart.

20. Apparatus as in claim 9, wherein the tank is embodied in material possessing insulating properties unaffected by chlorine.

* * * * *